(12) United States Patent
Kitajima

(10) Patent No.: US 7,027,220 B2
(45) Date of Patent: Apr. 11, 2006

(54) OPHTHALMOLOGIC OPERATION MICROSCOPE

(75) Inventor: Nobuaki Kitajima, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 0 days.

(21) Appl. No.: 10/862,451

(22) Filed: Jun. 8, 2004

(65) Prior Publication Data

US 2004/0257645 A1    Dec. 23, 2004

(30) Foreign Application Priority Data

Jun. 9, 2003    (JP) .............................. 2003-163931

(51) Int. Cl.
*G02B 21/00*    (2006.01)
(52) U.S. Cl. ........................ 359/381; 359/385; 351/216
(58) Field of Classification Search ................ 359/368, 359/381, 385; 351/205, 216, 217, 218, 219, 351/221

See application file for complete search history.

(56) References Cited

U.S. PATENT DOCUMENTS

| | | | |
|---|---|---|---|
| 3,664,730 A | | 5/1972 | Cardona ........................ 351/6 |
| 4,807,989 A | * | 2/1989 | Nagano et al. .............. 351/212 |
| 5,793,524 A | * | 8/1998 | Luloh .......................... 359/381 |
| 6,091,405 A | | 7/2000 | Lowe et al. ................. 345/175 |
| 6,788,455 B1 | * | 9/2004 | Kirchhuebel et al. ....... 359/381 |

FOREIGN PATENT DOCUMENTS

| | | |
|---|---|---|
| DE | 92 17 517.1 | 2/1993 |
| DE | 94 15 219.5 | 11/1994 |
| GB | 12885 | 5/1913 |
| JP | 2002-350735 | 12/2002 |

OTHER PUBLICATIONS

Copy of European Search Report dated Aug. 25, 2004, 2 pages.

* cited by examiner

*Primary Examiner*—Mark A. Robinson
(74) *Attorney, Agent, or Firm*—Armstrong, Kratz, Quintos, Hanson & Brooks, LLP

(57) ABSTRACT

Disclosed is an observation apparatus capable of eliminating in a suitable manner astigmatism and chromatic aberration generated in an observed image. The apex angle θ of a contact prism is input by operating an apex angle setting knob of a control panel, and the attachment angle thereof is input by operating an attachment angle setting knob. Based on the observation magnification recognized and the input apex angle θ, a control device determines the astigmatism correction amount for a left observation optical system and determines the astigmatism correction amount for the right observation optical system. Further, based on the input attachment angle, the axial angles of the astigmatisms of the left observation optical system and the right observation optical system are determined. Next, variable cross cylinder lens rotation drive devices are respectively controlled to rotate the respective cylinder lenses of the left and right observation optical systems to achieve the axial angle and correction amount as determined.

6 Claims, 9 Drawing Sheets

OPHTHALMOLOGIC OPERATION MICROSCOPE

BACKGROUND OF THE INVENTION

1. Field of the Invention

The present invention relates to an ophthalmologic operation microscope, and more particularly to an ophthalmologic operation microscope equipped with a front lens for observing the eyeground of the eye to be examined.

2. Description of the Related Art

Usually, an ophthalmologic operation is conducted with microscopic observation. JP2002-350735A (paragraph [0016]–[0018], FIG. 6, FIG. 7, and FIG. 9) discloses an example of a microscope for such ophthalmologic operation. In the ophthalmologic operation microscope as disclosed in the above publication, a front lens is arranged between the objective lens and the eye to be examined, making it possible to illuminate the interior of the eye. This enables the operator to perform operation, in particular, eyeground operation, with surgical instruments in both hands. As shown in FIGS. 6 and 9 of the above-mentioned publication, the front lens is detachably arranged between the objective lens and the eye.

Further, as shown in FIG. 7 of the above-mentioned publication, in the ophthalmologic operation microscope as disclosed therein, illumination light is applied to the eye through an illumination prism provided so as to be offset from the optical axis of the observation optical system.

When, however, illumination light is applied from a direction oblique to the optical axis of the observation optical system, there are observed two reflection images of the exit pupil of the illumination optical system due to the reflective action of the refraction surfaces of the front lens. That is, the front lens has two refraction surfaces, and, when seen from the direction of the optical axis of the observation optical system, the reflecting positions of the two refraction surfaces reflecting the exit pupil differ from each other, with the result that two reflection images are observed.

Such reflection images lead to deficiency in visual field for the operator and constitute light spots in the observation image, making it rather difficult to observe the portions around the same.

SUMMARY OF THE INVENTION

The present invention has been made in view of the above problem in the prior art. It is an object of the present invention to provide an ophthalmologic operation microscope that enables the operator to obtain a satisfactory visual field.

In order to achieve the above-mentioned object, according to a first aspect of the present invention, there is provided an ophthalmologic operation microscope including: an objective lens arranged so as to be opposed to an eye to be examined; an observation optical system composed of various optical elements and used to observe the eye through the objective lens; an illumination optical system applying illumination light to the eye from a direction at a predetermined angle with respect to an optical axis of the observation optical system; a front lens detachably provided between the eye and the objective lens; and an image position changing means for changing positions of two reflection images of an exit pupil of the illumination optical system, which are generated through reflection of the illumination light by two refraction surfaces of the front lens, so that the two reflection images may not obstruct observation.

Further, in order to achieve the above-mentioned object, according to a second aspect of the present invention, there is provided an ophthalmologic operation microscope in the first aspect of the invention, characterized in that the image position changing means changes the positions of the reflection images by arranging the front lens in an inclined state.

Further, in order to achieve the above-mentioned object, according to a third aspect of the present invention, there is provided an ophthalmologic operation microscope in the first aspect of the invention, characterized in that the image position changing means arranges the front lens so as to be at an acute angle with respect to an observation axis.

Further, in order to achieve the above-mentioned object, according to a fourth aspect of the present invention, there is provided an ophthalmologic operation microscope in the first aspect of the invention, characterized in that the image position changing means arranges the front lens so as to be at an obtuse angle with respect to an observation axis.

Further, in order to achieve the above-mentioned object, according to a fifth aspect of the present invention, there is provided an ophthalmologic operation microscope in the second aspect of the invention, characterized in that the observation optical system has left and right observation optical paths for respectively guiding observation light to the left and right eyes of an operator, and that the image position changing means arranges the optical axis of the front lens in a direction so as to substantially divide in two equal parts an angle made by a segment connecting a midpoint of centers of left and right entrance pupils corresponding to the left and right observation optical paths and a focus of the observation light due to the front lens and a segment connecting a center of the exit pupil of the illumination optical system and the focus.

In order to achieve the above-mentioned object, according to a sixth aspect of the present invention, there is provided an ophthalmologic operation microscope including: an objective lens arranged so as to be opposed to an eye to be examined; an observation optical system composed of various optical elements and used to observe the eye through the objective lens; an illumination optical system applying illumination light to the eye from a direction at a predetermined angle with respect to an optical axis of the observation optical system; a front lens detachably provided between the eye and the objective lens; and a shielding means for shielding a part of the illumination light reaching an area where reflection images of an exit pupil of the illumination optical system generated through reflection of the illumination light by two refraction surfaces of the front lens are to be observed.

Further, in order to achieve the above-mentioned object, according to a seventh aspect of the present invention, there is provided an ophthalmologic operation microscope in the sixth aspect of the invention, characterized in that the shielding means is arranged at a position optically conjugate with a point in an entrance pupil of the observation optical system with respect to the refraction surfaces of the front lens.

Further, in order to achieve the above-mentioned object, according to an eighth aspect of the present invention, there is provided an ophthalmologic operation microscope in the sixth or the seventh aspect of the invention, characterized in that the shielding means switches between shielding and transmission of a part of the illumination light according to whether the front lens is being used or removed.

Further, in order to achieve the above-mentioned object, according to a ninth aspect of the present invention, there is provided an ophthalmologic operation microscope in any one of the sixth to the eighth aspects of the invention, characterized in that the shielding means is a liquid crystal display arranged in the optical path of the illumination light and capable of displaying at a desired position a shielding area shielding the illumination light.

In order to achieve the above-mentioned object, according to a tenth aspect of the present invention, there is provided an ophthalmologic operation microscope including: an objective lens arranged so as to be opposed to an eye to be examined; an observation optical system composed of various optical elements and used to observe the eye through the objective lens; an illumination optical system applying illumination light to the eye from a direction at a predetermined angle with respect to an optical axis of the observation optical system; a front lens detachably provided between the eye and the objective lens; an image position changing means for changing positions of two reflection images of an exit pupil of the illumination optical system, which are generated through reflection of the illumination light by two refraction surfaces of the front lens, such that the two reflection images are substantially superimposed one upon the other when observed; and a shielding means for shielding a part of the illumination light reaching an area of the reflection images caused to be substantially superimposed one upon the other when observed by the image position changing means.

BRIEF DESCRIPTION OF THE DRAWINGS

FIGS. 2A through 2C are schematic enlarged views of the general construction of an operator microscope in an ophthalmologic operation microscope according to an embodiment of the present invention, in which FIG. 2A is an external side view, FIG. 2B is an external front view, and FIG. 2C is a see-through side view showing how a front lens is accommodated;

FIGS. 3A through 3C are enlarged views for illustrating the way the front lens is arranged in an ophthalmologic operation microscope according to an embodiment of the present invention, of which FIG. 3A is a see-through side view, FIG. 3B is a rear view, and FIG. 3C is an explanatory view illustrating how the front lens is arranged in an inclined state;

FIGS. 10A and 10B are enlarged views schematically showing the construction of a part of an ophthalmologic operation microscope according to another embodiment of the present invention, of which FIG. 10A is a side view and FIG. 10B is a see-through side view;

DETAILED DESCRIPTION OF THE PREFERRED EMBODIMENTS

An ophthalmologic operation microscope according to an embodiment of the present invention will now be described in detail with reference to the drawings.

[First Embodiment]

[General Construction of an Ophthalmologic Operation Microscope]

Figure 1:
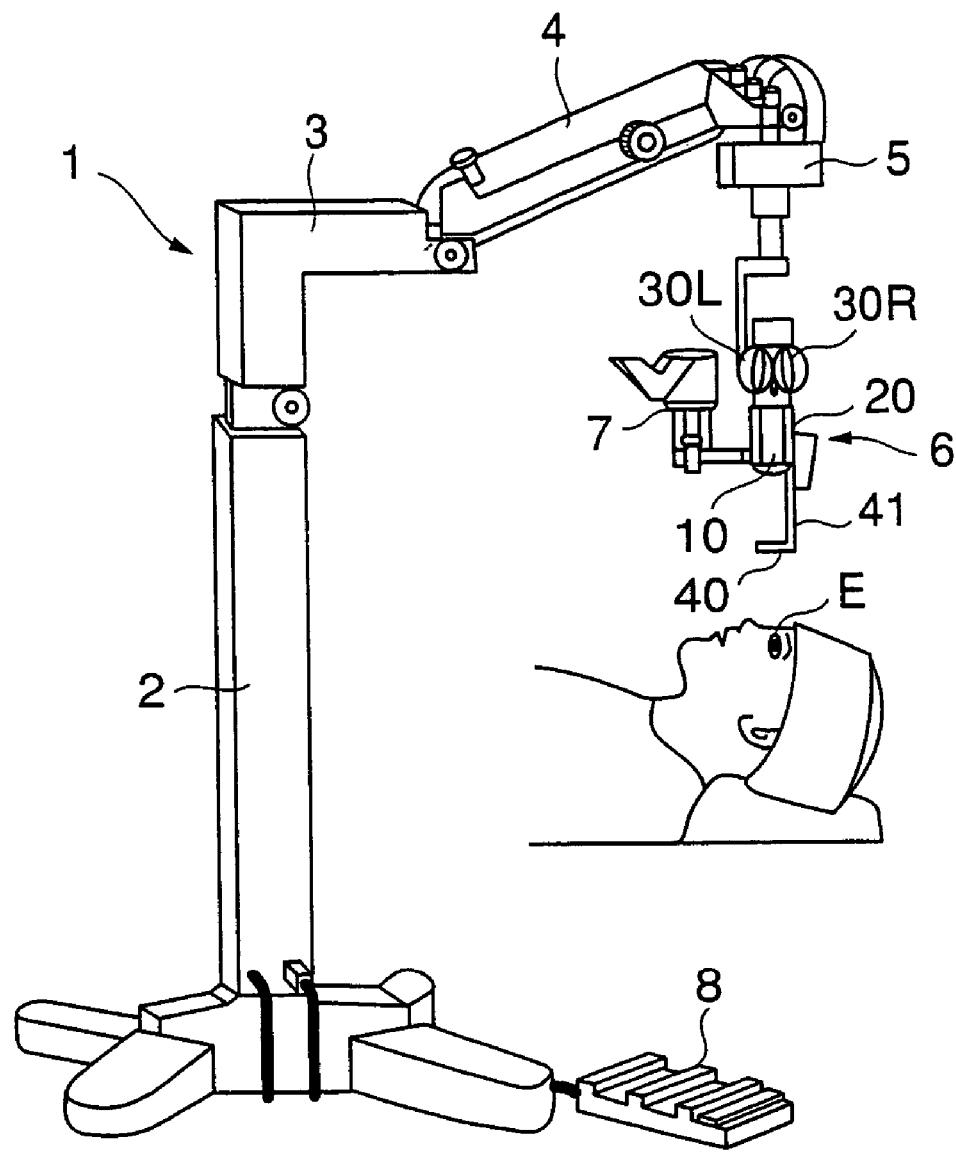
FIG. 1 is a schematic external view of the general construction of an ophthalmologic operation microscope according to an embodiment of the present invention.

FIG. 1 shows the general construction of an ophthalmologic operation microscope 1 according to the first embodiment. This ophthalmologic operation microscope 1 is equipped with a column 2 for supporting the apparatus, a first arm 3 one end of which is connected to the upper end of the column 2, a second arm 4 one end of which is connected to the other end of the first arm 3, a drive device 5 connected to the other end of the second arm 4, an operator microscope 6 suspended from the drive device 5, an assistant microscope 7 disposed adjacent to the operator microscope 6, and a foot switch 8 for performing various operations with a foot. The operator microscope 6 and the assistant microscope 7 are driven three-dimensionally, i.e., vertically and horizontally, by the drive device S. Symbol E indicates an eye of the patient who is subjected to operation. Numeral 40 indicates a front lens disposed between the objective lens of the operator microscope 6 (described below) and the eye E.

[Construction of the Operator Microscope]

Figure 2A:
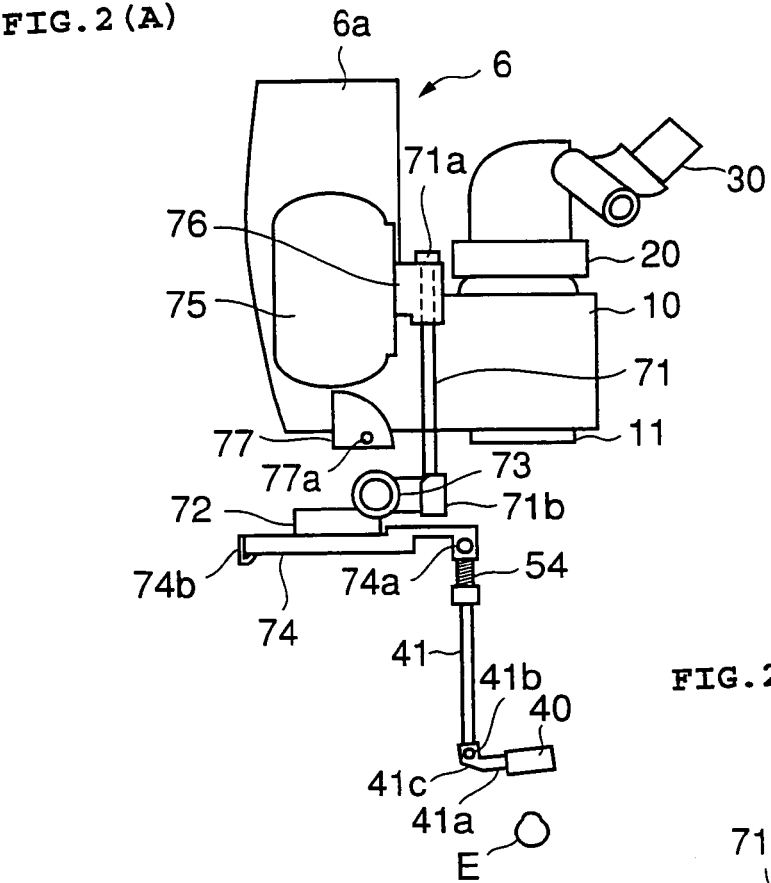
Figure 2B:
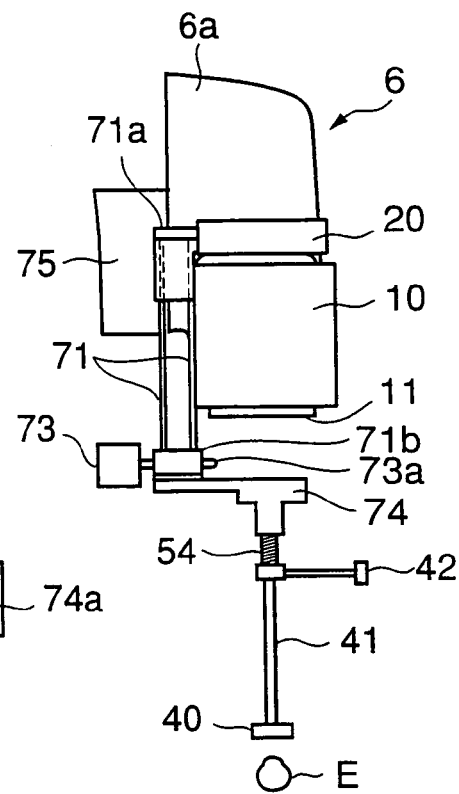
Figure 2C:
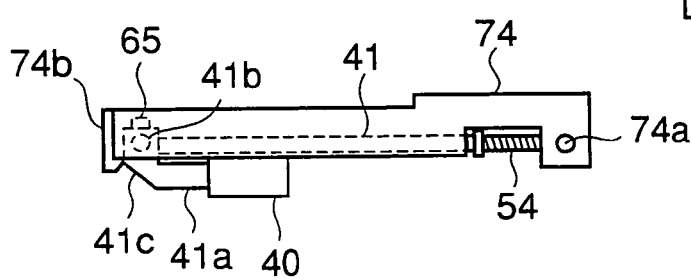

FIGS. 2A through 2C are enlarged views for illustrating the construction of the operator microscope 6. FIG. 2A is an external side view, FIG. 2B is an external front view, and FIG. 2C is a see-through side view showing how the front lens is accommodated. As shown in these drawings, the operator microscope 6 is equipped with a main body portion 6a, a lens barrel portion 10, an inverter portion 20, and a pair of eyepieces 30 (30L and 30R). In FIG. 2B, the eyepieces 30 are omitted. The front lens 40 is connected to the lens barrel portion 10 through the intermediation of a retaining arm 41, etc., and is detachably provided between the objective lens and the eye E (as described in detail below).

Although not shown, the main body portion 6a accommodates a control circuit for performing operation control on the operator microscope 6, a drive device for effecting vertical fine adjustment of the barrel portion 10 by the control circuit, etc. The lens barrel portion 10 accommodates an optical system (described below), inclusive of the objective lens 11, for illuminating and observing the eye E. The inverter portion 20 accommodates a well-known optical unit for converting an inverted image as observed into an erect image.

[Construction of the Front Lens and the Periphery thereof]

Next, the construction of the front lens 40 and the periphery thereof will be described. As stated above, the front lens 40 is connected to the operator microscope 6 through the intermediation of the retaining arm 41, etc. The front lens 40 is mounted to a retaining plate 41a formed at the distal end of the retaining arm 41.

The retaining arm 41 and the retaining plate 41a are rotatably connected together by an axle 41b. The retaining plate 41a is equipped with a beveled portion 41c. The retaining arm 41 is equipped with a front lens operating knob 42 for swinging the retaining arm 41.

The operator microscope 6 further includes an ascent/descent arm 71 with a fringe portion 71a at its top, a connection portion 71b connected to the lower portion of the ascent/descent arm 71, an ascent regulating member 72 connected to the connection portion 71b, a connection knob 73 passed through the connection portion 71b, and an accommodating portion 74 detachably mounted to the ascent regulating member 72 and serving to accommodate the front lens 40 and the retaining arm 41. The retaining arm 41 is pivoted to the accommodating portion 74 by an axle 74a. Further, a coil spring 54 is mounted to the top portion of the retaining arm 41. The reason for making the accommodating portion 74 detachable with respect to the ascent regulating member 72 is that it has to be detached therefrom after operation, etc. in order to sterilize the front lens 40 and the retaining arm 41. Even with the front lens 40, etc. removed there from, the microscope can be used as an ordinary operation microscope. In the following, the members mentioned in this paragraph may be collectively referred to as the front lens support portion.

The main body portion 6a of the operator microscope 6 is equipped with a drive portion 75 for vertically driving an ascent/descent arm support member 76 supporting the ascent/descent arm 71. The ascent/descent arm 71 is passed through the ascent/descent arm support member 76. Further, due to the presence of the fringe portion 71a, the ascent/descent arm 71 is prevented from being detached and dropping from the ascent/descent arm support member 76. Thus, as the ascent/descent arm 76 is vertically moved by the drive portion 75, the front lens 40 is vertically moved, thereby changing its position relative to the objective lens 11. Due to this arrangement, independently of the fine vertical adjustment of the lens barrel portion 10, it is possible to vertically move the front lens 40 alone.

Further, mounted to the lower portion of the main body portion 6a is an ascent regulating member 77 for regulating, together with the ascent regulating member 72, the upward movement range of the front lens support portion. Formed in this ascent regulating member 77 is a connection hole 77a for connecting and securing the front lens support portion to the main body portion 6a by operating the connection knob 73. To connect the front lens support portion to the main body portion 6a, the front lens support portion is raised to the uppermost position by the drive portion 75 (At this time, a protrusion 73a of the connection knob 73 and the connection hole 77a are mated with each other), and the connection knob 73 is rotated in a predetermined direction to fit the protrusion 73a into the connection hole 77a.

FIGS. 2A and 2B show the front lens 40 of the operator microscope 6 in the state in which the lens has been inserted between the eye E and the objective lens 11 (i.e., when it is being used). When the use of the front lens 40 is stopped and the front lens is to be retracted, the operator grips a front lens operating knob 42 and upwardly swings the retaining arm 41 around the axle 74a, whereby the front lens 40 and the retaining arm 41 are accommodated in the accommodating portion 74. Conversely, to bring the front lens 40 accommodated in the accommodating portion 74 into the state of use, the retaining arm 41 is swung downwards in a similar fashion.

Figure 3A:
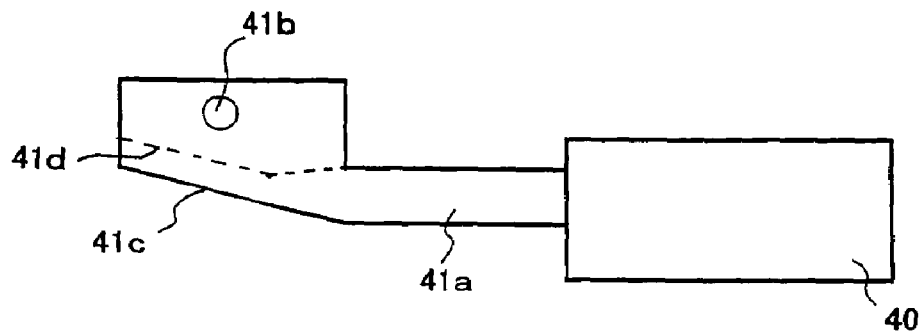
Figure 3B:
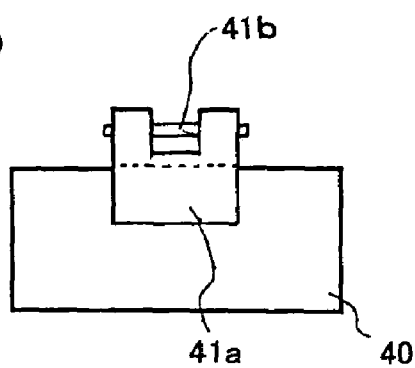
Figure 3C:
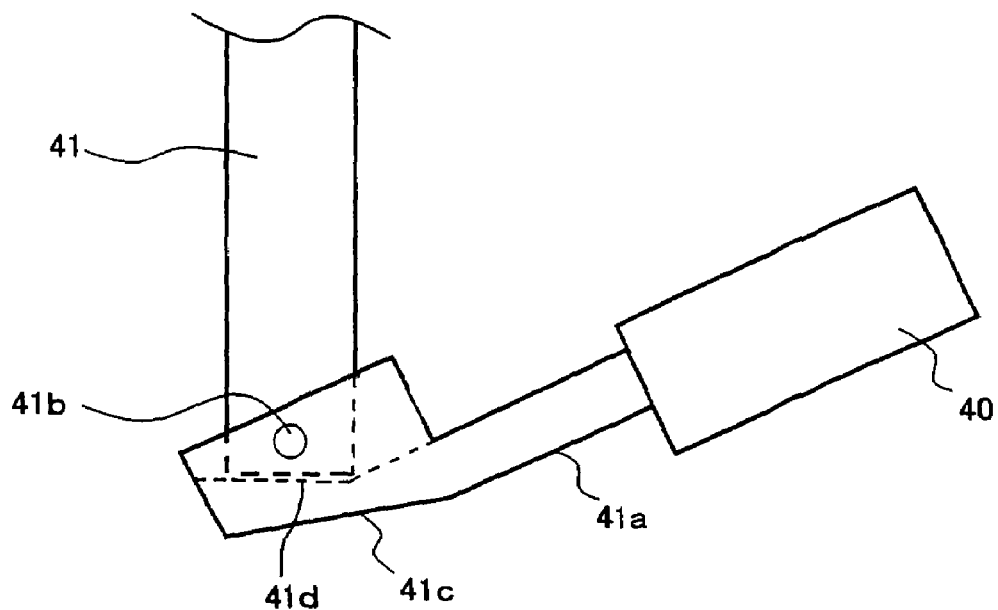

As shown in FIG. 2A, when it is being used, the front lens 40 is arranged such that its optical axis is directed at a predetermined angle with respect to the optical axis direction (vertical direction) of the objective lens 11. This inclined arrangement of the front lens 40 is realized by the construction as shown in FIGS. 3A through 3C. In FIGS. 2A thorough 3C, the inclination of the front lens 40 is somewhat exaggerated for clarity of illustration.

FIG. 3A is a see-through side view schematically showing the construction of the front lens 40 and the retaining plate 41a, FIG. 3B is a schematic view of the front lens 40 and the retaining plate 41a as seen from the left side in FIG. 3A, and FIG. 3C is an explanatory view showing how the front lens 40 is arranged in an inclined state when in use.

Figure 11A:
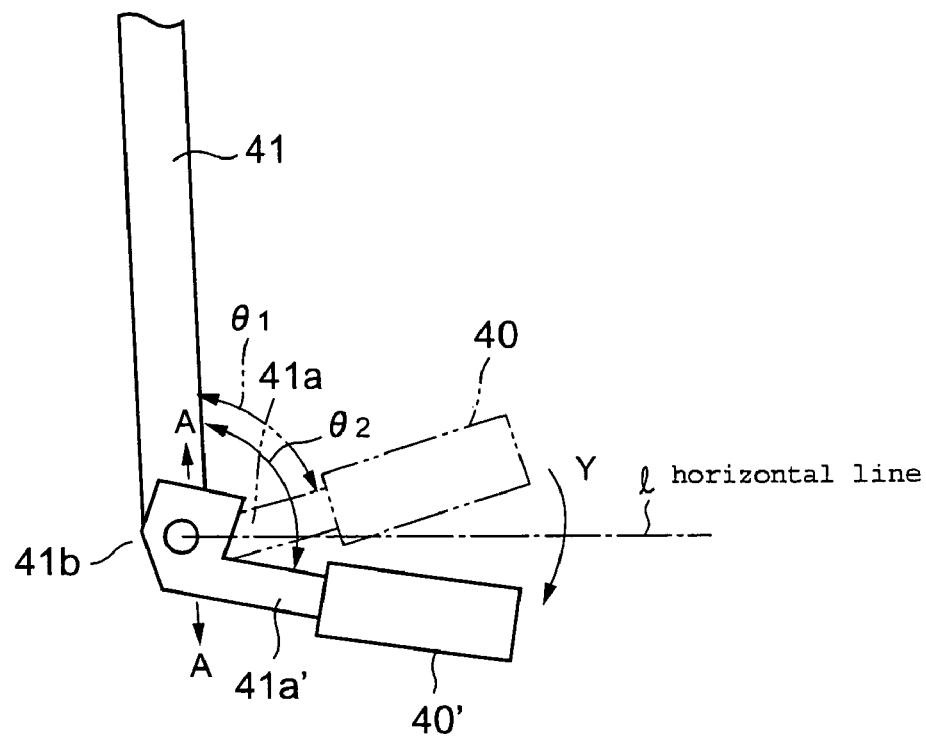
FIG. 11A is an explanatory view showing the construction of a main portion of an ophthalmologic operation microscope according to a third embodiment of the present invention.
Figure 11B:
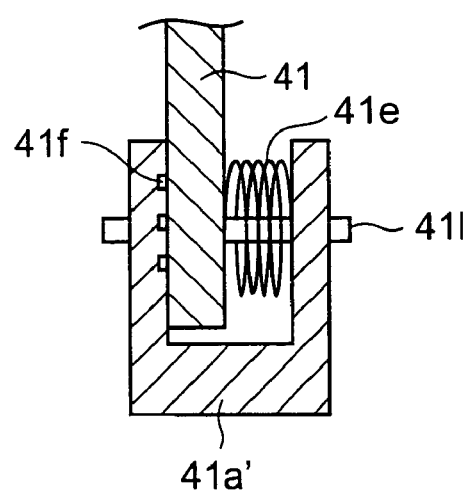
FIG. 11B is a sectional view taken along the line A–A of FIG. 11A.

As shown in FIG. 3B, the retaining plate 41a has a U-shaped portion, and the lower end portion of the retaining arm 41 is inserted into the region surrounded by the U-shaped portion, for example, as shown in FIG. 11(B), pivoted and elastically retained. Accordingly, the retaining plate 41a can be held at the desired inclination angle as shown in a virtual line 41d of FIG. 3(C). As will be described in detail below, these retaining arm 41 and retaining plate 41a constitute what is referred to as an image position changing means in the present invention.

As shown in FIG. 3C, when the retaining plate 41a thus formed is used, the rotating operation of the retaining plate 41a with respect to the retaining arm 41 arranged vertically is regulated by the elastic holding force, so that the front lens 40 is arranged in an inclined state.

FIG. 2C shows the front lens 40 as accommodated in an accommodating portion 74 (accommodated position). As shown in the drawing, the front lens 40 and the retaining arm 41 upwardly swung around the axle 74a are accommodated so as to extend in the longitudinal direction of the accommodating portion 74. Further, the retaining plate 41a is rotated around the axle 41b, and accommodated in a folded state. This is due to the action of the beveled portion 41c of the retaining plate 41a and a contact member 74b mounted to an end of the accommodating portion 74; when the retaining arm 41 is swung upwards, the beveled portion 41c comes into contact with the contact member 74b, and the retaining plate 41a is rotated around the axle 41b while being guided by the beveled portion 41c to be automatically folded before being accommodated. Further, the accommodating portion 74 is equipped with a micro switch 65 for detecting whether the front lens 40 is accommodated or not; when the front lens 40 is accommodated in the accommodating portion 74, a part of the retaining plate 41a comes into contact with the micro switch to turn it on, and, when the accommodation is canceled, the contact state is also canceled, and the switch is turned off. The operation of this micro switch 65 will be illustrated with reference to a variation described below.

[Construction of the Optical System]

Figure 4:
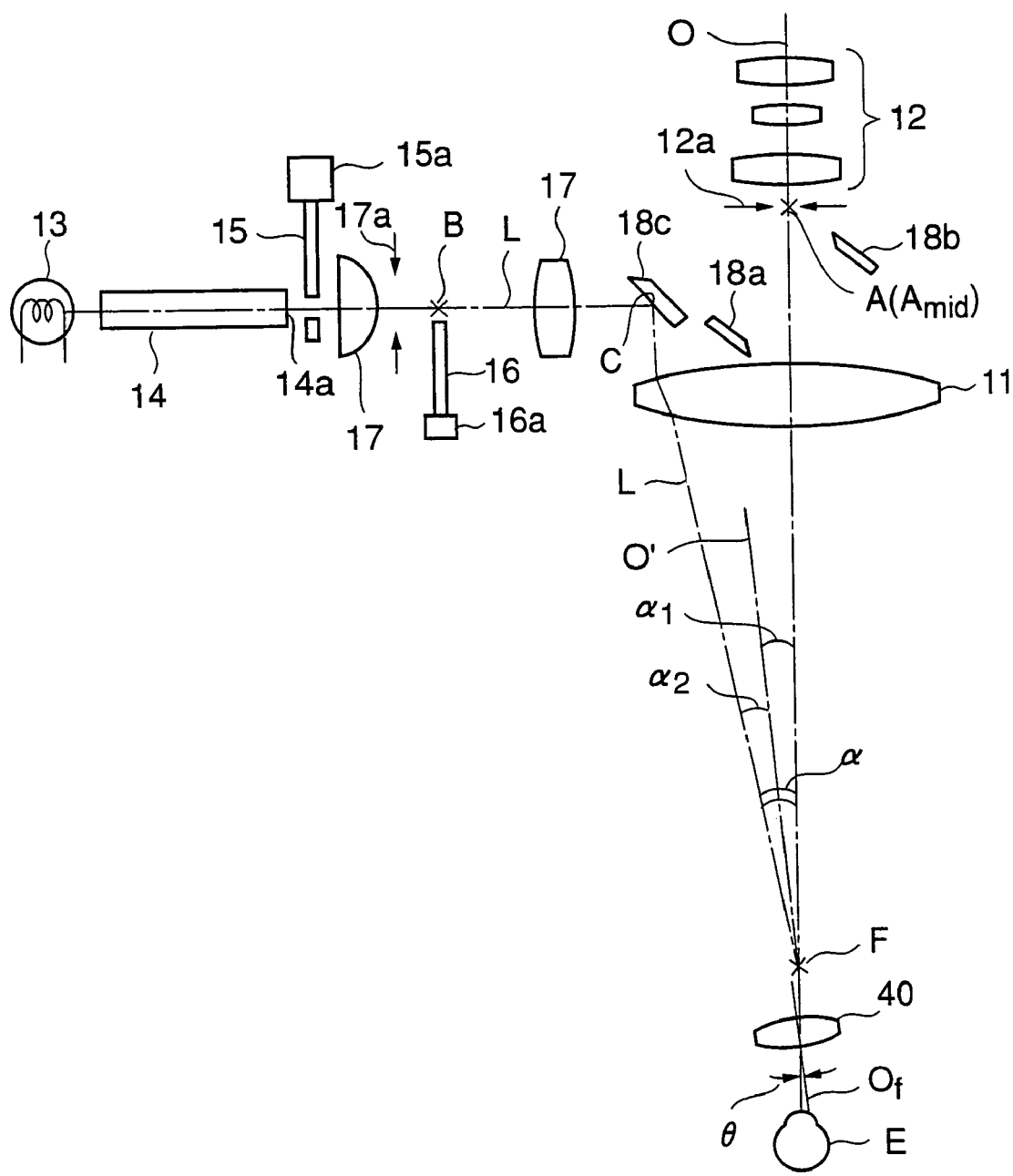
FIG. 4 is a schematic side view showing the construction of an optical system of an ophthalmologic operation microscope according to an embodiment of the present invention.
Figure 5:
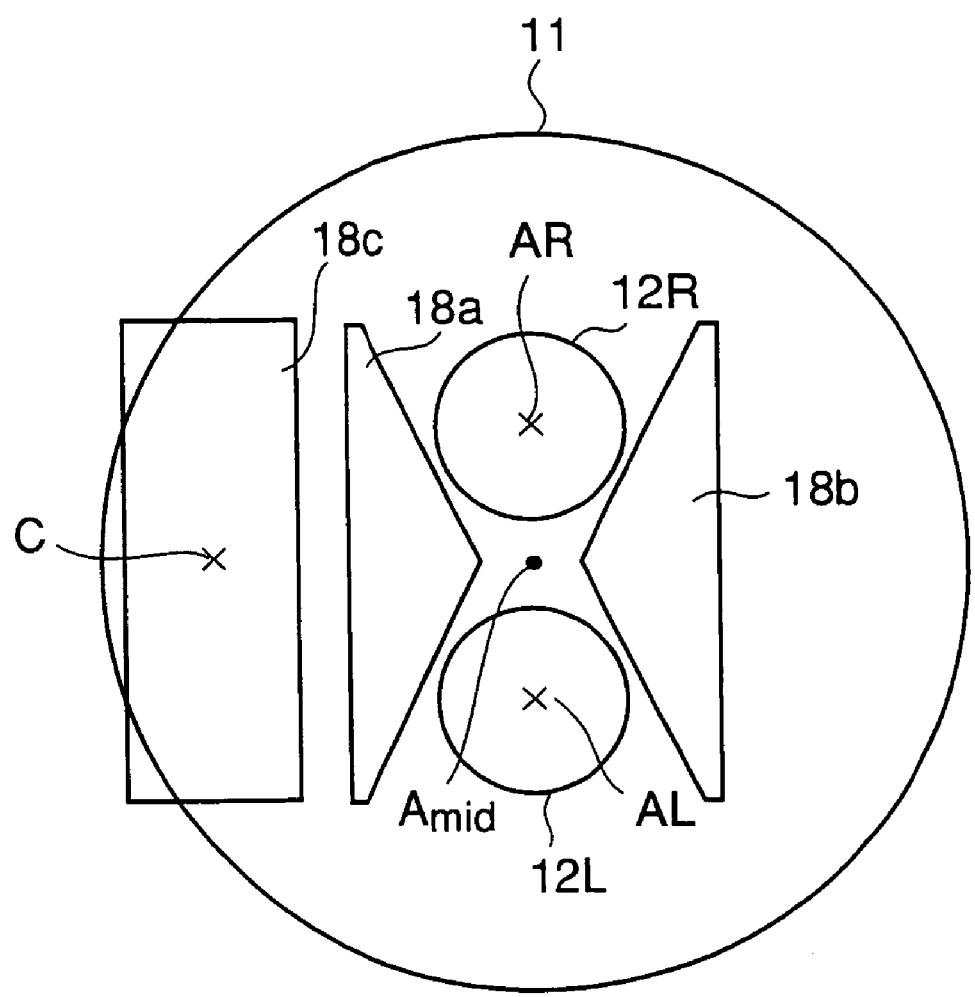
FIG. 5 is a top view schematically showing the construction of a part of the optical system of an ophthalmologic operation microscope according to an embodiment of the present invention.
Figure 6:
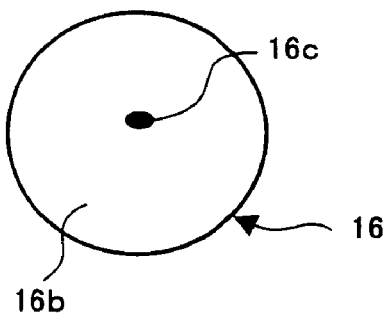
FIG. 6 is a schematic diagram showing the structure of a shielding member of an ophthalmologic operation microscope according to an embodiment of the present invention.

Next, the optical system accommodated in the barrel portion 10 of the operator microscope 6 will be described with reference to FIGS. 4, 5 and 6. FIG. 4 is a side view schematically showing the construction of this optical system. FIG. 5 is a top view schematically showing the construction of a part of this optical system. FIG. 6 is a diagram schematically showing the construction of a shielding member 16 described below.

As shown in FIG. 4, provided in the lens barrel portion 10 are an objective lens 11, an observation optical system 12, a light source 13, a light guide 14, a shielding plate 15, a shielding member 16, a lens unit 17, a diaphragm 17a, and deflection mirrors 18a, 18b, and 18c. The light source 13, the light guide 14, the shielding plate 15, the shielding member 16, the lens unit 17, the diaphragm 17a, and the deflection mirrors 18a, 18b, and 18c constitute what is referred to as an illumination optical system in the present invention. Further, although not shown, the lens barrel portion 10 also contains an imaging means, such as a CCD device, for photographing an observation image of the eye E. In the following, photographing by such an imaging means will also be considered as a form of observation.

Further, between the eye E and the objective lens 11, there is arranged the front lens 40 in use in a state in which the lens is inclined by a predetermined angle. Here, observation light from the eye E forms a focus F between the front lens 40 and the objective lens 11. Thus, the eye E is observed as an inverted image; however, it is observed after being converted to an erect image by the optical unit in the inverter 20, so that the requisite operability during operation is ensured.

In the extension of the optical axis of the objective lens 11, there are arranged the eyepieces 30L and 30R for the left and right eyes (see FIG. 1) for the operator to observe the eye E. The observation optical system 12 is composed of a pair of observation optical systems 12L and 12R as shown in FIG. 5, and the observation optical systems 12L and 12R are composed of lens units including variable-power lenses for varying observation power, guiding observation light to the left and right eyepieces 30L and 30R. In FIG. 4, numeral 12a indicates an entrance pupil of the observation optical system 12.

The light guide 14 is formed with a bundle of optical fibers guiding illumination light from the light source 13. The shielding plate 15 is an optical member arranged adjacent to an exit end 14a of the light guide 14 and adapted to shield a part of the illumination light from the exit end 14a, thereby making it possible to apply illumination light having a desired cross-sectional configuration. The shielding plate 15 is constructed so as to make it possible to selectively arrange light transmission areas of various configurations in the optical path for the illumination light by means of a shielding plate drive mechanism 15a consisting of a stepping motor or the like. The configuration of the light transmission area of the shielding plate 15 is selected according to the deflection mirror 18a, 18b, or 18c that is used.

The shielding member 16 constitutes what is referred to as the shielding means in the present invention, and consists, for example, of an optical member as shown in FIG. 6 which is adapted to shield a part of the illumination light having passed the shielding plate 15. This shielding member 16 is put in and out of the optical path of the illumination light by a shielding member drive means 16a consisting of a solenoid or the like. This operation can be effected, for example, by the foot switch 8. The shielding member 16 shown in FIG. 6 is a plate-like optical member formed of a plastic material or the like, and has a light transmitting area 16b transmitting illumination light and a shielding area 16c not transmitting illumination light. The position of this shielding area 16c will be discussed below.

Further, the shielding member 16 is arranged such that, in an optical system in which a point A in the entrance pupil 12a of the observation optical system 12 (e.g., the center thereof) constitutes the object point and in which the front lens 40 constitutes the reflection surface, the shielding member is inserted at the position of a point B which is optically conjugate with respect to the object point.

The lens unit 17 guides the illumination light transmitted through the light transmission area 16b of the shielding member 16 to a position in the vicinity of the optical axis of the observation optical system 12 (observation optical axis). The diaphragm 17a serves to restrict the area of the eye E to be illuminated, and is provided at a position conjugate with the focus F.

The deflection mirrors 18a, 18b, and 18c consist of reflection members arranged at predetermined positions above the objective lens 11 and in the vicinity of the observation optical axis, and serve to deflect the illumination light guided by the lens unit 17 and to guide it toward the eye E through the objective lens 11.

Next, the construction of the observation optical system 12 and its periphery will be described with reference to FIG. 5. As stated above, the observation optical system 12 consists of the left observation optical system 12L and the right observation optical system 12R; the left observation optical system 12L guides observation light to the eyepiece 30L for the left eye, and the right observation optical system 12R guides observation light to the eyepiece 30R for the right eye.

The deflection mirrors 18a, 18b, and 18c have configurations as shown in FIG. 5. The light transmission areas of the shielding plate 15 have configurations respectively corresponding to the configurations of the deflection mirrors 18a, 18b, and 18c.

The deflection mirrors 18a and 18b are used when the red reflex (diaphanographic image) of the eye E is to be obtained. More specifically, the light transmission areas of the shielding plate 15 are appropriately selected to guide illumination light simultaneously to both the deflection mirrors 18a and 18b, whereby it is possible to illuminate the eye E from a small height with respect to the observation optical axis and from both sides. This makes it possible to obtain the red reflex over the entire observation area of the retina of the eye E.

The illumination light applied by way of the deflection mirror 18c is at a larger angle with respect to that in the case of the deflection mirrors 18a and 18b, so that it is used when a sense of perspective is desired in the observation image.

In the following, the case will be described in which illumination light is applied by way of the deflection mirror 18c as shown in FIG. 4. The following description also applies to the case in which the other reflection mirrors are used.

In FIG. 5, symbols AL and AR respectively indicate the centers of the entrance pupils of the left observation optical system 12L and the right observation optical system 12R. The midpoint of the entrance pupils AL and AR will be indicated by symbol $A_{mid}$. In the drawing, symbol C indicates the center of the entrance pupil of the illumination optical system when the deflection mirror 18c is being used.

When seen sidewise, the arrangement of the midpoint $A_{mid}$ of the entrance pupils AL and AR of the left and right observation optical systems 12L and 12R and a center C of the exit pupil of the illumination optical system is as shown in FIG. 4. That is, the illumination light from the light source 13 travels by way of the optical elements of the illumination optical system and is reflected by the area of the deflection mirror 18*c* including the center C of the exit pupil to illuminate the eye E through the objective lens 11 and the front lens 40. The illumination light reflected by the eye E travels through the front lens 40 as observation light to temporarily form the focus F. Then, the light travels by way of the objective lens 11 and is transmitted through the entrance pupils AL and AR of the left and right observation optical systems 12L and 12R to be guided to the eyepieces 30L and 30R.

Here, the segment passing the midpoint $A_{mid}$ of the entrance pupils AL and AR and the focus F will be referred to as the observation axis O, and the segment in the angular direction when the illumination light reflected by the center C of the exit pupil passes the focus F will be referred to as an illumination axis L. Further, the angle made by an observation axis O and the illumination axis L will be referred to as $\alpha$, and the segment dividing this angle $\alpha$ substantially into two equal parts will be referred to as a segment O'. That is, the angle $\alpha_1$ is substantially equal to an angle $\alpha_2$. Here, an inclination angle $\theta$ of an optical axis $O_f$ of the front lens 40 with respect to the observation axis O is set to $\alpha_1$.

[Operation and Effects]

Figure 7A:
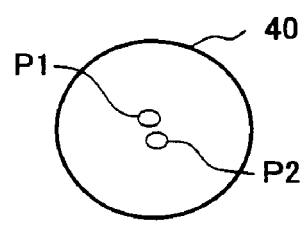
FIGS. 7A and 7B are schematic diagrams showing how eye observation is performed by a conventional ophthalmologic operation microscope.
Figure 7B:
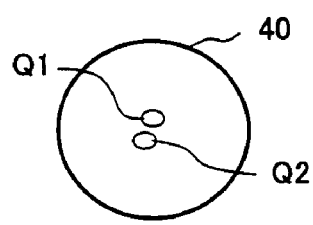
Figure 8A:
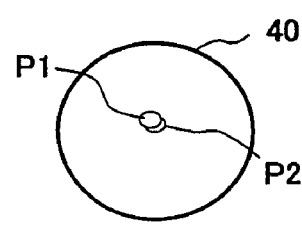
FIGS. 8A and 8B are schematic diagrams showing how eye observation is performed by an ophthalmologic operation microscope according to an embodiment of the present invention.
Figure 8B:
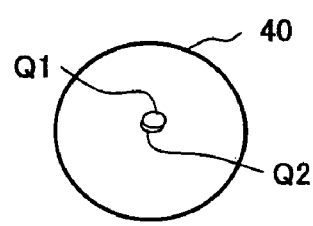
Figure 9A:
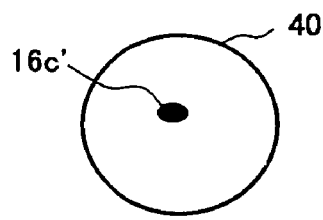
FIGS. 9A and 9B are schematic diagrams showing how eye observation is performed by an ophthalmologic operation microscope according to an embodiment of the present invention.
Figure 9B:
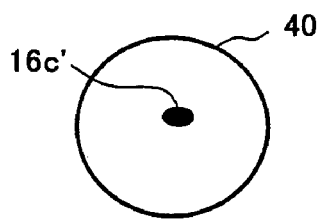

In the following, the operation and effects of the ophthalmologic operation microscope 1, constructed as described above, will be described with reference to FIGS. 7A through 9B. FIGS. 7A and 7B schematically show how the eye E is observed in the conventional system, in which the optical axis $O_f$ of the front lens 40 coincides with the observation axis O, with no inclination angle therebetween. FIGS. 8A and 8B schematically show how the eye E is observed according to the present invention, in which the front lens 40 is inclined with respect to the observation axis O. FIGS. 9A and 9B schematically show how observation is performed when the shielding member 16 is caused to operate in the case of FIGS. 8A and 8B, in which the front lens 40 is inclined. Of these drawings, FIGS. 7A, 8A, and 9A show how observation is performed through the left observation optical system 12L and FIGS. 7B, 8B, and 9B show how observation is performed through the right observation optical system 12R.

First, the conventional system shown in FIGS. 7A and 7B will be described. When the optical axis $O_f$ of the front lens 40 coincides with the observation axis O, due to the angle $\alpha$ made by the illumination axis L and the observation axis O, the exit pupil of the illumination optical system forms two reflection images by the two refraction surfaces of the front lens 40. Here, the two reflection images observed through the left observation optical system 12L will be referred to as left reflection images P1 and P2, and the two reflection images observed through the right observation optical system 12R will be referred to as right reflection images Q1 and Q2. When the angle $\alpha$ is of a magnitude normally selected, the left reflection images P1 and P2 and the right reflection images Q1 and Q2 are observed apart from each other. Thus, the left observation image of the eye E is encroached upon by the two light spots formed by the left reflection images P1 and P2, with the result that the area that can be observed is reduced. Further, the portions around the two light spots suffer deterioration invisibility due to their dazzling. Similarly, the right observation image of the eye E suffers a reduction in the area allowing observation and deterioration in visibility in the portions around the light spots.

In contrast, in the ophthalmologic operation microscope 1 of the present invention, the optical axis $O_f$ of the front lens 40 is inclined with respect to the observation axis O by the above-mentioned angle $\theta$, so that, as shown in FIGS. 8A and 8B, the left reflection images P1 and P2 and the right reflection images Q1 and Q2 are respectively superimposed one upon the other when observed. Thus, the area of the observation image encroached upon by them is reduced (substantially by half), and the area that allows observation is enlarged as compared with that in the related art, thus achieving an improvement in terms of observing condition.

Despite the improvement in observing condition through substantial coincidence of the two reflection images, the visibility of the portion around the reflection images is not yet to be considered as satisfactory. To eliminate this adverse influence, the shielding member driving means 16*a* is operated to put the shielding member 16 in the optical path of the illumination light.

Here, the shielding region 16*c* of the shielding member 16 is positioned so as to shield the cross-sectional region of the illumination light reaching the position of the left reflection images P1 and P2 and the right reflection images Q1 and Q2, which are substantially superimposed one upon the other when observed. Thus, the illumination light for forming each reflection image is partially shielded, so that, as shown in FIGS. 9A and 9B, the positions corresponding to the left and right reflection images are observed as dark points 16*c*' where no illumination light strikes. Thus, deterioration is eliminated in visibility due to the dazzling of the portions around the points 16*c*', which are dark points (that is, the portions around the regions where the reflection images should be present).

It is desirable that the shielding region 16*c* of the shielding member 16 be formed in such a size as will form a dark point slightly larger than the two reflection images substantially superimposed one upon the other when observed. The position of the shielding region 16*c* in the shielding member 16 is determined uniquely according to the inclination angle of the front lens 40, so that it can be previously set at an appropriate position.

While only the case has been illustrated in which the illumination light is reflected by the deflection mirror 18*c* to illuminate the eye E, what has been described is also applicable to the case in which observation is performed with the deflection mirrors 18*a* or 18*b* by adopting a construction allowing the inclination angle of the front lens 40 to be changed stepwise. Assuming that the angle made at this time by the illumination axis and the observation axis O is $\beta$, the front lens 40 is inclined such that its optical axis $O_f$ is at an angle of approximately $\beta/2$ with respect to the observation axis O. Thus, it is only necessary for the optical axis $O_f$ of the front lens 40 to be changed in position stepwise so as to be at $\alpha_1$ or $\beta/2$ with respect to the observation axis O.

Further, it is not always necessary for the inclining direction of the optical axis $O_f$ of the front lens 40 to be substantially ½ of the angle made by the illumination axis L and the observation axis O; it can be appropriately set according to the conditions, such as the device specifications and the individual differences between devices.

[Modifications]

While in the above-described embodiment switching between use and non-use of the shielding member 16 is effected by operating the foot switch 8, it is also possible to adopt a construction in which switching is effected in correspondence with use/non-use of the front lens 40. For example, as shown in FIG. 2C, the micro switch 65 is provided for detecting whether the front lens 40 is placed in the accommodation position or not (as described above).

When the front lens 40 is released from the accommodation position and the micro switch 65 is turned off, a control circuit (not shown) provided in the main body portion 6a of the operator microscope 6 transmits a control signal to the shielding member driving means 16a to cause the shielding member 16 to be put in the optical path of the illumination light. Conversely, when the front lens 40 is set in the accommodation position and the micro switch 65 is turned on, the control circuit transmits a control signal to the shielding member driving means 16a to cause the shielding member 16 to retract from the optical path of the illumination light. Due to this construction, it is possible to set or remove the shielding member 16 in correspondence with use/non-use of the front lens 40, which is convenient from the viewpoint of practical use.

[Second Embodiment]

Figure 10A:
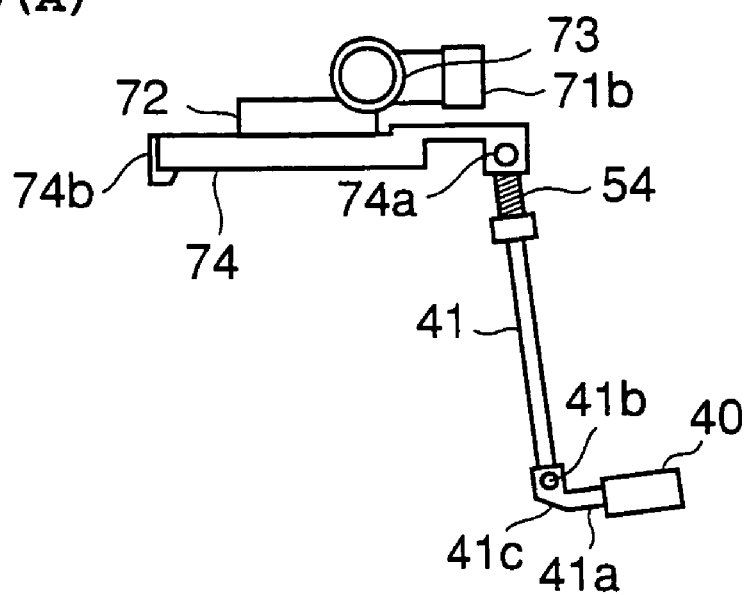
Figure 10B:
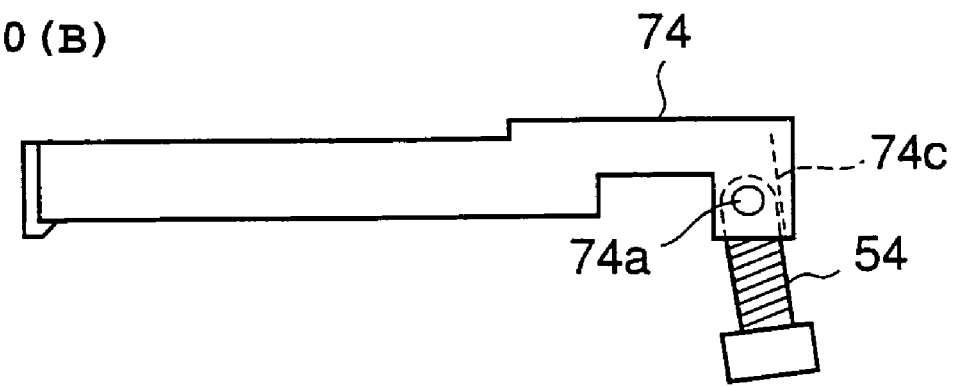

Next, another embodiment of the present invention will be described. This embodiment differs from the first embodiment in the construction for inclining the front lens. In the following description, the components that are the same as those of the first embodiment will be indicated by the same reference numerals. FIGS. 10A and 10B schematically show the construction of a part of the ophthalmologic operation microscope of this embodiment.

FIG. 10A shows the front lens 40 in the state of use. The ophthalmologic operation microscope of this embodiment is characterized by the construction of the accommodating portion 74 and the connection portion connected with the coil spring 54. The accommodating portion 74 and the coil spring 54 are rotatably connected by an axle 74a. By swinging the retaining arm 41, switching between use and non-use of the front lens 40 is effected. The portion where the accommodating portion 74 and the coil spring 54 are connected with each other is formed such that when the front lens 40 is being used, the retaining arm 41 is at a predetermined angle with respect to the vertical direction. To achieve such an inclination angle, there is adopted, for example, a construction as shown in FIG. 10B, in which an inclined wall surface 74c is formed inside the accommodating portion 74, with the rotation of the coil spring 54 in the direction of the position of use being restricted by this wall surface 74c. In this case, by adapting the inclination angle of the wall surface 74c with respect to the vertical direction to an appropriate inclination angle of the front lens 40, it is possible to obtain the same effect as that in the first embodiment. It is to be noted here that, in FIGS. 10A and 10B, the inclination angle of the front lens 40 is exaggerated to clarify the illustration.

While two specific constructions for inclining the front lens 40 have been disclosed with reference to the first and second embodiments, it is possible to obtain the same effect as that of these embodiments by any other construction as long as it is a construction that causes the front lens 40 to incline with respect to the observation axis O.

[Third Embodiment]

While in the first and second embodiments described above the front lens 40, which is inclined, is arranged above the horizontal line, it is also possible to obtain the same effect as that of the first and second embodiments by inclining the front lens 40 so as to be situated below the horizontal line 1 as shown in FIG. 11A.

The third embodiment will be described in more detail. As indicated by the chain line in FIG. 11A, in the first and second embodiments, the front lens 40 is inclined so as to be situated above the horizontal line 1, which is at the level of the axle 41b (that is, such that the angle $\theta_1$ made by the retaining arm 41 (or observation axis) and the retaining plate 41a is an acute angle). In this embodiment, in contrast, the front lens 40', indicated by the solid line, is rotated in the direction of the arrow Y so as to be situated below the horizontal line 1 (that is, such that the angle $\theta_2$ made by the retaining arm 41 (or observation axis) and the retaining plate 41a' is an obtuse angle). To thus allow rotation between the acute angle $\theta_2$ and the obtuse angle $\theta_2$, there is adopted, as shown in FIG. 11B, a construction in which a click engagement through elastic contact is effected by a plurality of (at least two) recesses and protrusions 41f provided at the portion (in the vicinity of the axle 41b) where the retaining arm 41 and the front lens retaining plate 41a' are connected and by a spring 41e. Alternatively, it is also possible to adopt a construction in which a wire is passed through the retaining arm 41, with the lower end of the wire being fixed to the front lens retaining plate 41a, and in which the upper end of the wire is mounted to the apparatus main body through the intermediation of a pulley or the like, the operation being conducted manually. In the third embodiment, the above construction for effecting click engagement or wire connection constitutes the image position changing means.

Figure 12A:
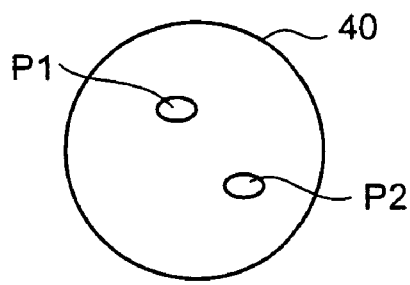
FIGS. 12A and 12B are schematic diagrams showing the effects of the third embodiment of the present invention.
Figure 12B:
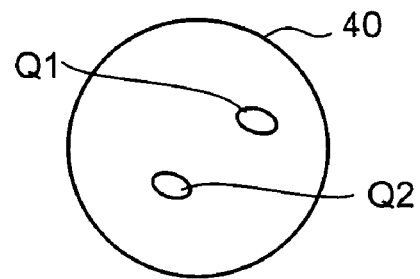

Next, the effect of the construction in which, as in the third embodiment, the front lens 40 is inclined so as to be situated below the horizontal line 1 will be illustrated with reference to FIGS. 12A and 12B. Since the front lens 40 is inclined so as to be situated below the horizontal line 1, the left reflection images P1 and P2 and the right reflection images Q1 and Q2 are respectively observed at positions spaced apart from each other as shown in FIGS. 12A and 12B. As a result, the central area requisite for observation is enlarged, thereby achieving an improvement in terms of observation efficiency as in the first and second embodiments.

[Fourth Embodiment]

Figure 13A:
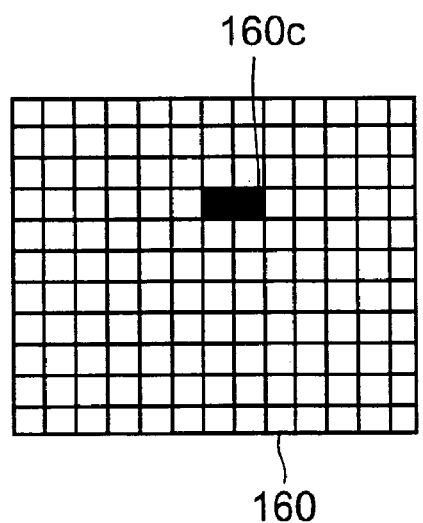
FIGS. 13A and 13B are diagrams schematically showing the construction of a shielding member in an ophthalmologic operation microscope according to fourth embodiment of the present invention.
Figure 13B:
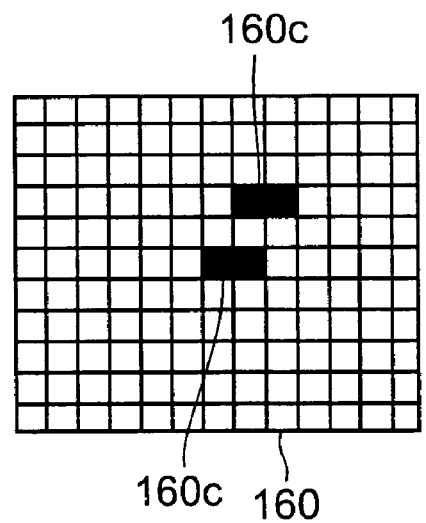

Next, still another embodiment of the present invention will be described. This embodiment employs a shielding member different from that of the first embodiment. FIGS. 13A and 13B schematically show the construction of an example of the shielding member 160 of this embodiment. The shielding member 160 is a liquid crystal display (LCD) provided in the optical path of the illumination light; when nothing is being displayed, the illumination light is allowed to pass through it. Further, the shielding member 160 by LCD is controlled so as to be capable of displaying a black shielding area 160c at an arbitrary position by the above-mentioned control circuit. For example, it is possible to form a shielding area 160c consisting of a single area as shown in FIG. 13A, or form a shielding area 160c consisting of two separate areas as shown in FIG. 13B.

Use of the shielding member 160 by LCD as the shielding member provides the following effects. First, when the front lens 40 is arranged in an inclined state and the two reflection images of the exit pupil of the illumination optical system as observed are substantially matched with each other, one shielding area 160c is displayed at the position on the shielding member 160 by LCD corresponding to the position of the reflection images, as shown in FIG. 13A, to form a dark point in the observation image. When the front lens 40 is not inclined and two reflection images are to be observed, shielding areas are respectively displayed at the positions on the shielding member 160 by LCD corresponding to the positions of these two reflection images to thereby form two dark points.

Thus, according to this embodiment, even when the position of the reflection image is changed as a result of a change in the incident height of the illumination light, etc., it is possible to appropriately change the position of the shielding area. Further, even when the front lens is not inclined, it is possible to turn the areas corresponding to the two reflection images into dark points, thereby achieving an improvement in terms of visibility.

Further, it is also possible to adopt an arrangement in which the position on the shielding member 160 by LCD where the shielding area is displayed is changed in conformity with the position where the reflection image is observed by the above-mentioned control circuit (when the number of reflection images is one and/or two) With this arrangement, even if the position of the reflection image is changed, a dark point is automatically formed at that position, which is convenient from the viewpoint of practical use.

The constructions described in detail above only constitute examples of how the present invention is to be carried out, and it goes without saying that various modifications and additions in terms of construction are possible without departing from the scope of the present invention.

According to one aspect of the present invention, it is possible to change the positions of the two reflection images of the exit pupil of the illumination optical system due to the front lens such that they are substantially superimposed one upon the other when observed, whereby it is possible to enlarge the area that allows observation. Thus, the operator can obtain a satisfactory visual field.

According to another aspect of the present invention, it is possible to shield a part of illumination light to be applied to the area where the reflection images of the exit pupil of the illumination optical system are observed, so that it is possible to eliminate a deterioration in visibility due to the dazzling of the reflection images, thereby providing a satisfactory visual field.

What is claimed is:

1. An ophthalmologic operation microscope comprising:
    an objective lens arranged so as to be opposed to an eye to be examined;
    an observation optical system composed of various optical elements and used to observe the eye to be examined through the objective lens;
    an illumination optical system applying illumination light to the eye to be examined from a direction at a predetermined angle with respect to an optical axis of the observation optical system;
    a front lens detachably provided between the eye to be examined and the objective lens; and
    an image position changing means for changing positions of two reflection images of an exit pupil of the illumination optical system, the two reflection images being generated through reflection of the illumination light by two refraction surfaces of the front lens and observed.

2. An ophthalmologic operation microscope according to claim 1, wherein the image position changing means changes the positions of the reflection images by arranging the front lens in an inclined state.

3. An ophthalmologic operation microscope according to claim 2, wherein the observation optical system has left and right observation optical paths for respectively guiding observation light to the left and right eyes of an operator, and
    wherein the image position changing means arranges the optical axis of the front lens in a direction so as to substantially divide in two equal parts an angle made by a segment connecting a midpoint of centers of left and right entrance pupils corresponding to the left and right observation optical paths and a focus of the observation light due to the front lens and a segment connecting a center of the exit pupil of the illumination optical system and the focus.

4. An ophthalmologic operation microscope according to claim 1, wherein the image position changing means arranges the front lens so as to be at an acute angle with respect to an observation axis.

5. An ophthalmologic operation microscope according to claim 1, wherein the image position changing means arranges the front lens so as to be at an obtuse angle with respect to an observation axis.

6. An ophthalmologic operation microscope comprising:
    an objective lens arranged so as to be opposed to an eye to be examined;
    an observation optical system composed of various optical elements and used to observe the eye to be examined through the objective lens;
    an illumination optical system applying illumination light to the eye to be examined from a direction at a predetermined angle with respect to an optical axis of the observation optical system;
    a front lens detachably provided between the eye to be examined and the objective lens;
    an image position changing means for changing positions of two reflection images of an exit pupil of the illumination optical system, which are generated through reflection of the illumination light by two refraction surfaces of the front lens, such that the two reflection images are substantially superimposed one upon the other when observed; and
    a shielding means for shielding a part of the illumination light reaching an area of the reflection images caused to be substantially superimposed one upon the other when observed by the image position changing means.

* * * * *